United States Patent [19]

Schnepp-Pesch et al.

[11] Patent Number: 5,116,352
[45] Date of Patent: May 26, 1992

[54] APPARATUS FOR REMOVING DEPOSITS FROM VESSELS

[75] Inventors: Wolfram Schnepp-Pesch, Ettlingen; Josef Lindenberg, Karlsruhe, both of Fed. Rep. of Germany

[73] Assignee: Angiomed AG, Karlsruhe, Fed. Rep. of Germany

[21] Appl. No.: 589,588

[22] Filed: Sep. 28, 1990

[30] Foreign Application Priority Data

Oct. 6, 1989 [DE] Fed. Rep. of Germany ... 8911909[U]
Oct. 6, 1989 [DE] Fed. Rep. of Germany ... 8911911[U]
Oct. 6, 1989 [DE] Fed. Rep. of Germany ... 8911912[U]

[51] Int. Cl.⁵ .............................................. A61B 17/32
[52] U.S. Cl. .................................. 606/171; 606/170; 604/22
[58] Field of Search ............... 604/22; 606/128, 129, 606/169, 170, 171, 172

[56] References Cited

U.S. PATENT DOCUMENTS

| 4,167,944 | 9/1979 | Banko | 606/170 |
| 4,649,914 | 3/1987 | Thinson et al. | 606/170 |
| 4,850,957 | 7/1989 | Summers | 604/22 |
| 4,979,939 | 12/1990 | Shiber | 606/170 |

Primary Examiner—Francis Jaworski
Assistant Examiner—Scott R. Akers
Attorney, Agent, or Firm—Antonelli, Terry, Stout & Kraus

[57] ABSTRACT

An apparatus for removing deposits, such as plaque, in vessels and atherosclerotically transformed wall areas. The apparatus includes a rotary wire and a working coil which extends on the front end of the rotary wire. A ball is provided on a distal end of the working coil; additionally, sharp cutting edges are provided on the ball for engaging and cutting the deposits. The ball is able to rotate eccentrically with respect to a longitudinal axis of symmetry of the working coil.

11 Claims, 1 Drawing Sheet

APPARATUS FOR REMOVING DEPOSITS FROM VESSELS

Field of the Invention

The invention relates to an apparatus for removing deposits, such as plaque in vessels, atherosclerotically transformed wall portions, etc., with a working coil at the front end of a rotary wire and which is provided at its distal end with a ball.

The term front end is used to define the end of the particular part inserted in the body first, i.e. towards the interior of the patient's body and distal with respect to the surgeon.

An apparatus of the aforementioned type is known from German Utility Model 89 00 971. The known apparatus operates in a largely satisfactory manner, but improvements are desirable particularly relative to the use of such an apparatus for atherectomy.

Whereas in the case of the apparatus of German Utility Model 89 00 971 plaque and in particular solid, rigid plaque, is removed by the striking of the coil or helix in the vicinity of the deposits, in the case of the tough atherosclerotically transformed wall areas this does not occur to the desired extent.

SUMMARY OF THE INVENTION

The aim underlying of the invention, essentially reaches in developing an apparatus of the aformentioned type, in such a way that even in the case of the tougher atherosclerotically transformed wall portions it permits a controlled, circumferentially symmetrical removal of material increasing the flow resistance in the vessel. According to the invention this problem is solved in an apparatus of the aforementioned type in that the ball is provided with sharp edges.

As a result of the sharp-edged construction of the outer circumference of the ball it is possible to reliably and rapidly remove in controlled cutting manner the atherosclerotically transformed wall areas of vessels and in particular, blood vessels, which could only take place in an inferior manner and required a longer time in the case of the known vessel through the mere striking of the working coil or the correspondingly constructed distal end. In addition, as a result of the inventive construction a controlled symmetrical dilation of the vessel can be obtained. In connection with the construction of the drive of a corresponding inventive apparatus, the passage of the drive shaft through a catheter or the like, express reference is made to German Utility Model 89 00 971, whose disclosure is expressly formed into part of the disclosure of the present utility model. As a result of the inventive construction of the apparatus, material removed from the vessel can be suctioned out in per se known manner using the aforementioned catheter.

According to a preferred construction, the sharp edges are formed by the rear transition edge between the outer casing of the ball, considered in the rotation direction of the latter and the boundary wall of a slot formed in the ball under an acute angle to the tangent on the outer wall. As a result of the acute angle formed by the cutting edge between the outer circumference of the ball or a tangent thereon and the inner wall of the slot forming the cutting edge with the outer circumference, tissue deposits are peeled off without there being any risk of deep incisions in the living vessel tissue. This avoids dissection or antegrad undercut pockets.

The solution of the set problem by the above measures is also assisted if the outside of the working coil or helix has a sharp edge. With regards to the effects and advantages, what was stated hereinbefore regarding the sharp-edged ball construction applies.

According to preferred further developments of the outer edge of the working coil, the sharp edge is formed by the grinding of the outer region of the coil or the sharp edge is formed by squeezing or crushing the outer region of the coil. The sharp edges can be provided either in the case of an apparatus in which the working coil is formed by a helically guided wire, or in which the working coil is formed by a blade multiply twisted about its longitudinal axis.

In order to obtain a large radial working area for the removal of deposits in vessels in the case of small puncture sites, the ball is, according to the invention, positioned eccentrically to the rotary wire axis. This can be achieved by slight bending of the working coil or the eccentric arrangement of the ball.

As a result of the eccentric guidance of the ball fitted to the working coil at the end remote from the surgeon, a controlled enlargement of the working diameter from the coil diameter to virtually double this amount is achieved, without it being necessary to increase the size of the puncture site compared with the guide catheter diameter necessary for the passage of the coil. This guidance also improves the control of the abrasion of the wall portions. The risk of dissection or antegrad pocket formation in the vicinity of the vessel walls is reduced or eliminated.

According to a further development of the invention the ball has a bore parallel to the axis of symmetry of the working coil, but eccentrically thereto and through it extends a stationary held guide wire. The working diameter is extended over and beyond the working coil diameter to virtually double the amount thereof and the entire operating material and, in particular, the catheter through which the coil is introduced into the vessel can continue to have a small lumen or internal diameter. With an unmodified catheter and correspondingly unchanged small puncture sites, as a result of said construction it is possible to obtain a larger lumen opening in the vessel than would be possible with the prior art apparatus. Thus, according to the invention, the passage to be widened can be increased over and beyond the cross-section of the operating material in the way which was only previously possible in a complicated manner by the inflation of balloon catheters.

BRIEF DESCRIPTION OF THE DRAWINGS

Further advantages and features of the invention can be gathered from the claims and the following description, which explains in detail embodiments of the invention with reference to the drawings. The individual, preferred embodiments of the invention are shown in different drawings and separately explained to facilitate understanding and can obviously be substantially jointly realized on an object.

DETAILED DESCRIPTION

Figure 1:
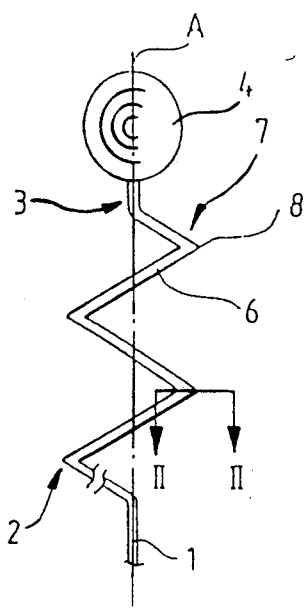
FIG. 1 is shown a first embodiment of the inventive apparatus with a working coil provided on its outside with a sharp edge.

FIGS. 1 to 7 show inventive constructions of the distal working ends of an apparatus for removing deposits, such as plaque in vessels, atherosclerotically transformed wall portions thereof, etc., as known from German Utility Model 89 00 971. An inventive apparatus has a drive shaft or a guide wire 1, on whose distal end is constructed a working coil or helix 2, whose distal end 3 is blunted to ensure that it cannot cause injury, either by a corresponding bending over and guiding back of a wire forming the coil 2, as disclosed in the aforementioned Utility Model, or by a ball 4 placed on the front end of the wire 1. The drive shaft or guide wire has an adequate strength to ensure a controlled guidance of the ball 4 rotating eccentrically about the drive shaft or guide wire 1. For use purposes the drive shaft 1 regularly extends through a hollow guide part, such as a plastic catheter (not shown), which can have two lumens. Within the guide catheter and optionally on the shaft 1 a screw thread helix can be connected in rotary manner to the shaft 1 for moving removed plaque particles from the distal end 3 through the guide part (catheter) to its proximal end and out of the same, e.g. via a branch, which can be connected to a suction device. The proximal, i.e. the surgeon-facing end of the drive shaft 1 projects out of the proximal end of the hollow guide part and is preferably fixed to the driven shaft of a motor, which drives the drive shaft 1 and therefore the working coil 2. This construction is not shown in detail in the drawings, because it is already explained in Utility Model 89 00 971, to which express reference is made.

Figure 2:
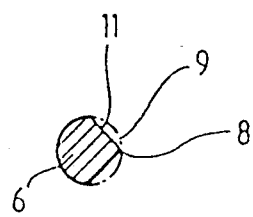
FIG. 2 is a section corresponding to II—II in FIG. 1 for showing the outer edge construction.
Figure 3:
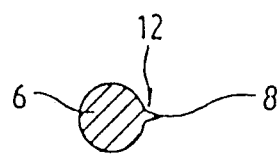
FIG. 3 is a corresponding section with a differently constructed outer edge.

In the construction according to FIG. 1, the working coil 2 is formed from a wire 6 bent helically over several turns and which, as can be gathered from FIGS. 2 and 3, can fundamentally be a round wire. The wire 6 and therefore the working coil 2 is provided on its outside 7 with a sharp working edge 8. The latter can be formed in that the round wire 6 is ground sharp on one side in such a way that tearing portions 9 are ground from it, when considering the cross-section and the remaining chords 11 (when considering the cross-section) forming the outer wall taper into a sharp outer edge 8. The chords 11 can form on the edge 8 a right angle, but preferably there is an acute angle. This can in particular be obtained in that the wire 6 is compressed or crushed along one longitudinal side to an edge forming in cross-section a point 12 as shown in FIG. 3. Fundamentally the round wire can be replaced by a flat wire for forming a working wire helix, the narrow sides of the wire being directed towards or away from the working coil axis of symmetry A and, in particular, the outer narrow side can be formed once again into a sharp edge, e.g. by grinding or crushing.

Figure 4:
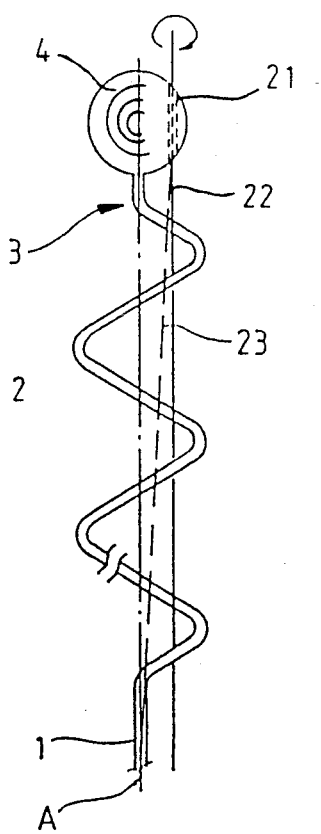
FIG. 4 is an embodiment of the invention with an assymmetrical guide wire passing through the distal ball.
Figure 5:
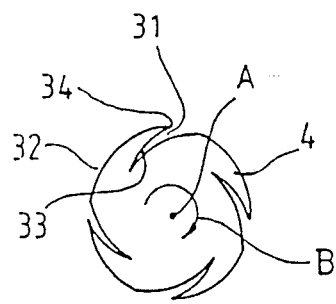
FIG. 5 is a distal working ball provided with cutting edges in plan view corresponding to arrow V in FIG. 6.

In FIG. 4 the ball 4 fixed to the distal end 3 of the working coil 2, has a bore 21 running parallel to the axis of symmetry A of the working coil, but eccentrically with respect thereto and through which extends a guide wire 22, which is also guided by the individual turns of the coil eccentrically to the axis thereof. During the driving of the working coil 2 via the drive shaft 1 the guide wire 21 ensures that the ball does not rotate about its center axis (which coincides with the axis of symmetry A of the working coil 2), but instead rotates eccentrically about the guide wire 21. Thus, the working coil 2 acquires a rotation axis 23, shown in broken line in FIG. 4 and which in the vicinity of the drive shaft 1 passes into the latter and therefore the axis of symmetry A of the working coil 2, but in the vicinity of the ball 4 passes into the guide wire 22 and in the intermediate area of the coil 2 between the two of them, i.e. between the axis of symmetry A and the guide wire 22. Thus, the working channel of the working coil 2 is enlarged or widened, which reduces or eliminates the risk of dissection or antegrad pocket formation. This leads to an improved, controlled abrasion of the wall portions, particularly in conjunction with the construction of FIGS. 1 to 3. Compared with the helix diameter, the working diameter is increased to twice the diameter of the maximum radial spacing from the outside of the coil to the guide wire 22 and simultaneously the introduced operating material remains as small a lumen as possible, i.e. a small puncture site can be reached with a large-lumen working channel.

Figure 6:
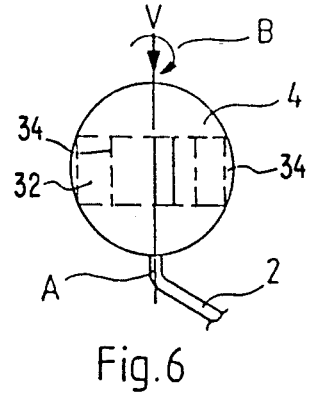
FIG. 6 is a side view of the ball of FIG. 5 in the direction of arrow VI in FIG. 5.

In the construction of FIGS. 4 and 6 the distal ball 4 is provided over a portion of its height parallel to the axis of symmetry A of the working coil 2 with incisions 31 at a finite angle to its radii emanating from the axis of symmetry A, so that a sharp cutting edge 34 is formed in the rear transition area with respect to the rotation direction B between the outer wall 32 and the wall 33 defining the incision. On rotating the ball 4 via the drive shaft 1 in the direction of arrow B the edge 34 engages on the deposits, plaque, etc., in the vessel and peels them off. As a result of the spherical surface of the ball 4, apart from the incisions 31, and the relatively acute angle of the cutting edge 34 with respect to the ball surface 32 deep cuts are avoided and the cutting process is limited to a gentle peeling effect.

Figure 8:
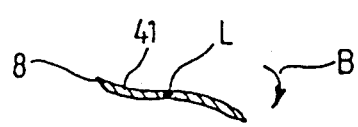
FIG. 8 is a section corresponding to VIII—VIII in FIG. 7 through the working coil in order to illustrate the sharp outer edges.
Figure 7:
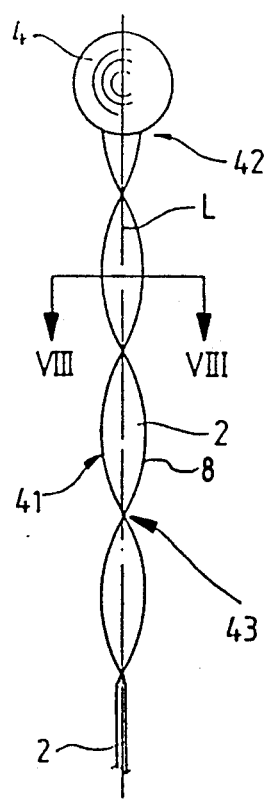
FIG. 7 is a view of another working coil construction, which can also have sharp outer edges.

FIGS. 7 and 8 show another construction in which the working coil 2 is formed by a blade 41 multiply helically wound about its longitudinal axis L and on whose distal end 42 is once again fixed a ball 4, while the working coil 2 is connected in its proximal area 43 to the drive shaft 1. Also with such a working coil 2 formed from a blade 41, sharp outer edges 8 can be provided and which, due to the rotation direction D of the coil 2, move the detached plaque material through the coil 2 to the drive shaft 1, with the edges being slightly bent in the working direction, so that they also act under a finite angle on the deposits to be removed, in much the same way as the edges 34 in the construction of FIGS. 5 and 6.

We claim:

1. Apparatus for removing deposits, such as plaque in vessels, aterosclerotically transformed wall portions, the apparatus comprising a rotary wire, a working coil extending on a front end of the rotary wire, a ball provided on a distal end of the working coil, sharp cutting edges provided on said ball for engaging and cutting said deposits, and means for mounting said ball so as to enable said ball to rotate eccentrically with respect to a longitudinal axis of symmetry of said working coil.

2. Apparatus for removing deposits, such as plaque in vessels, aterosclerotically transformed wall portions, with a working coil extending on a front end of the rotary wire, and provided on its distal end with a ball, characterized in that the ball is provided with sharp edges, the sharp edges are formed by a rear transition edge, considered in the rotation direction of the ball, between an outer wall of the ball and a boundary wall of a slot formed in the ball at an acute angle to a tangent on the outer wall.

3. Apparatus according to one of claims 1 or 2, wherein the sharp cutting edges extend over only a part of a total diameter of the ball.

4. Apparatus according to claim 3, wherein an outer portion of the working coil includes a sharp cutting edge.

5. Apparatus according to one of claims 1 or 2 wherein the working coil is a helical wire.

6. Apparatus according to one of claims 1 or 2, wherein the working coil is formed as a blade having a plurality of twists with respect to a longitudinal axis of the blade.

7. Apparatus according to claim 2 wherein means are provided for enabling a rotation of the ball eccentrically to a longitudinal center axis of the rotary wire.

8. Apparatus according to claim 7, wherein the working coil is curved.

9. Apparatus according to claim 7, wherein said means for enabling includes a bore provided in said ball and extending in parallel to an axis of symmetry of the working coil, and a stationarily held guide wire extending through said bore.

10. Apparatus according to claim 1, wherein said means for mounting said ball includes a bore provided in said ball and extending in parallel to an axis of symmetry of the working coil, and a stationarily held guide wire extending through said bore.

11. Apparatus according to claim 1, wherein an outer portion of the working coil includes a sharp cutting edge.

* * * * *